(12) United States Patent
Ajima

(10) Patent No.: US 10,867,418 B2
(45) Date of Patent: Dec. 15, 2020

(54) APPARATUS AND SYSTEM FOR GENERATING A CROSS-SECTIONAL ABDOMINAL IMAGE

(71) Applicant: KYOCERA Corporation, Kyoto (JP)

(72) Inventor: Hiromi Ajima, Kawasaki (JP)

(73) Assignee: KYOCERA Corporation, Kyoto (JP)

( * ) Notice: Subject to any disclaimer, the term of this patent is extended or adjusted under 35 U.S.C. 154(b) by 135 days.

(21) Appl. No.: 16/091,406

(22) PCT Filed: Mar. 24, 2017

(86) PCT No.: PCT/JP2017/012060
§ 371 (c)(1),
(2) Date: Oct. 4, 2018

(87) PCT Pub. No.: WO2017/175607
PCT Pub. Date: Oct. 12, 2017

(65) Prior Publication Data
US 2019/0130608 A1    May 2, 2019

(30) Foreign Application Priority Data

Apr. 6, 2016 (JP) ................ 2016-076738

(51) Int. Cl.
*G06T 7/62* (2017.01)
*G06T 11/00* (2006.01)
*G01B 21/20* (2006.01)
*A61B 5/107* (2006.01)
*G01B 15/04* (2006.01)

(52) U.S. Cl.
CPC .......... *G06T 11/003* (2013.01); *A61B 5/1072* (2013.01); *A61B 5/1079* (2013.01);
(Continued)

(58) Field of Classification Search
CPC ..... G06T 11/003; G06T 7/62; G06T 2211/40; G06T 2207/30004; G06T 2207/10081;
(Continued)

(56) References Cited

U.S. PATENT DOCUMENTS 8,095,211 B2 * 1/2012 Tamura ................ A61B 5/0059
600/547
8,116,544 B2 * 2/2012 Masumoto ........... A61B 5/1075
378/1

(Continued)

FOREIGN PATENT DOCUMENTS

| JP | 2002-191563 A | 7/2002 |
|---|---|---|
| JP | 2010207339 A | 9/2010 |
| JP | 2012029767 A | 2/2012 |
| WO | 2014203539 A1 | 12/2014 |

OTHER PUBLICATIONS

JP 2001212111 Yamada et al., "Visceral fat measuring apparatus" (Published Aug. 7, 2001).*

*Primary Examiner* — Sheela C Chawan
(74) *Attorney, Agent, or Firm* — Studebaker & Brackett PC

(57) ABSTRACT

An apparatus for generating a cross-sectional abdominal image includes a memory for storing a cross-sectional abdominal image, a measuring unit for measuring an outline of an abdomen, and a controller configured to correct the cross-sectional abdominal image based on the outline of the abdomen measured by the measuring unit.

14 Claims, 11 Drawing Sheets

(52) U.S. Cl.
CPC ............ *G01B 15/04* (2013.01); *G01B 21/20* (2013.01); *G06T 7/62* (2017.01); *G06T 2207/10081* (2013.01); *G06T 2207/30004* (2013.01); *G06T 2211/40* (2013.01)

(58) Field of Classification Search
CPC ..... A61B 5/1072; A61B 5/1079; A61B 5/107; A61B 5/1077; G01B 21/20; G01B 15/04; G01B 5/025
USPC ....... 382/100, 131, 128, 132, 154, 162, 168, 382/172, 173, 181, 190, 199, 201, 203, 382/232, 254, 266, 285, 312, 317
See application file for complete search history.

(56) References Cited

U.S. PATENT DOCUMENTS

| | | | |
|---|---|---|---|
| 8,527,040 B2 * | 9/2013 | Murakawa | A61B 5/0537 600/547 |
| 9,867,569 B2 | 1/2018 | Ajima | |
| 2011/0235886 A1 * | 9/2011 | Kelly | A61B 6/482 382/132 |
| 2011/0295144 A1 | 12/2011 | Murakawa et al. | |
| 2014/0121564 A1 * | 5/2014 | Raskin | A61B 5/4872 600/587 |
| 2015/0262026 A1 * | 9/2015 | Kitamura | G06K 9/52 382/128 |
| 2016/0242695 A1 | 8/2016 | Ajima | |
| 2018/0078203 A1 | 3/2018 | Ajima | |

\* cited by examiner

| Record No | Time (sec) | Direction information (deg/sec) | Direction (deg) | Motion information (Moving amount) (cm) |
|---|---|---|---|---|
| R0 | 0 | 0.00 | 0.00 | 0.00 |
| R1 | t1 | 8.22 | 1.37 | 0.42 |
| ⋮ | ⋮ | ⋮ | ⋮ | ⋮ |
| R(n/4) | T(n/4) | 48.72 | 90 | 20.50 |
| ⋮ | ⋮ | ⋮ | ⋮ | ⋮ |
| R(n/2) | T(n/2) | 0.44 | 180 | 41.00 |
| ⋮ | ⋮ | ⋮ | ⋮ | ⋮ |
| R(n/2+a) | T(n/2+a) | 38.21 | 190.12 | 43.15 |

|  |  | Subcutaneous fat area (cm²) | | | | |
|---|---|---|---|---|---|---|
|  |  | ~50 | 51~100 | 101~150 | 151~200 | 201~ |
| Visceral fat area (cm²) | ~50 | P11 | P12 | P13 | P14 | P15 |
|  | 51~100 | P21 | P22 | P23 | P24 | P25 |
|  | 101~150 | P31 | P32 | P33 | P34 | P35 |
|  | 151~200 | P41 | P42 | P43 | P44 | P45 |
|  | 201~ | P51 | P52 | P53 | P54 | P55 |

APPARATUS AND SYSTEM FOR GENERATING A CROSS-SECTIONAL ABDOMINAL IMAGE

CROSS REFERENCE TO RELATED APPLICATION

This application claims priority to and the benefit of Japanese Patent Application No. 2016-076738 (filed on Apr. 6, 2016), the entire contents of which are incorporated herein by reference.

TECHNICAL FIELD

The present disclosure relates to an apparatus and a system for generating a cross-sectional abdominal image.

BACKGROUND

Computerized tomography (hereinafter, also referred to as "CT") is conventionally known as a method for measuring a fat area in an abdominal cross-section. Methods for displaying the measured fat in a visually recognizable manner are also known. For example, an apparatus for displaying a fat area in a circular shape is known.

SUMMARY

An apparatus for generating a cross-sectional abdominal image according to an embodiment includes a memory for storing a cross-sectional abdominal image, a measuring unit for measuring an outline of an abdomen, and a controller configured to correct the cross-sectional abdominal image based on the outline of the abdomen measured by the measuring unit.

A system for generating a cross-sectional abdominal image according to an embodiment includes a memory for storing a cross-sectional abdominal image, a measuring unit for measuring an outline of an abdomen, and a controller configured to correct the cross-sectional abdominal image based on the outline of the abdomen.

DETAILED DESCRIPTION

If the display of an apparatus deviates significantly from an actual abdominal cross-section, the display method has room for improvement. According to the present disclosure, an apparatus and a system for generating an improved cross-sectional abdominal image can be provided.

Embodiments will be described in detail with reference to the drawings.

According to the present embodiment, a smartphone 1 is used as an example of an apparatus, and a human abdomen is used as an example of an object.

The smartphone 1 serving as the apparatus measures (computes) an outline of a user's abdomen, corrects an outline of a cross-sectional abdominal image based on the measured outline of the abdomen, and then displays the corrected outline. The smartphone 1 estimates a visceral fat area and a subcutaneous fat area from a part of the measured outline of the abdomen. The smartphone 1 displays the cross-sectional abdominal image based on the estimated values of the visceral fat area and the subcutaneous fat area.

The smartphone 1 includes at least a first sensor for acquiring direction information, which will be described later, a device for acquiring motion information, and a controller (a control unit) 10 configured to calculate the outline of the abdomen serving as the object. According to the present embodiment, the device for obtaining the motion information includes a second sensor.

Figure 1:
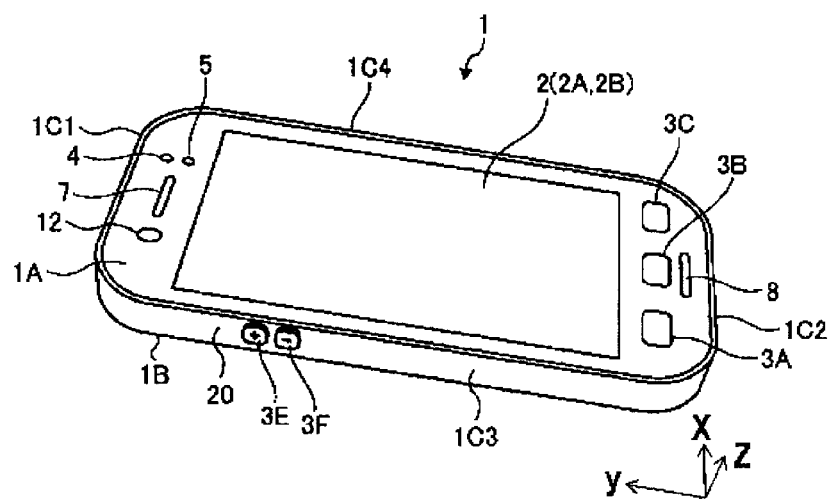
FIG. 1 is a perspective view schematically illustrating an exterior of a smartphone according to an embodiment.
Figure 2:
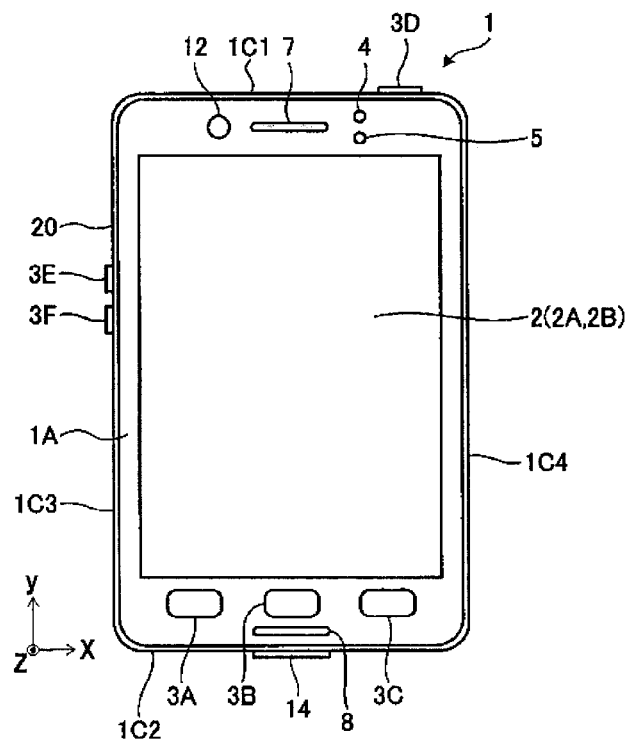
FIG. 2 is an elevation view schematically illustrating the exterior of the smartphone according to the embodiment.
Figure 3:
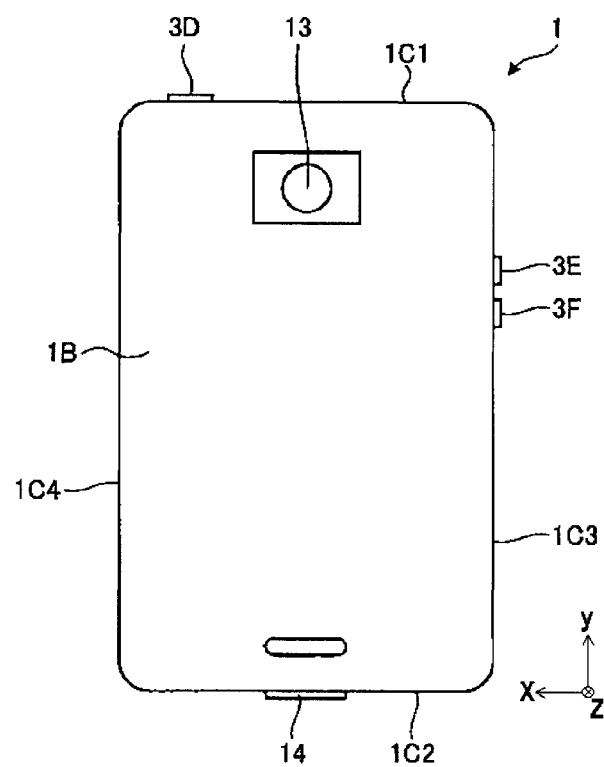
FIG. 3 is a rear view schematically illustrating the exterior of the smartphone according to the embodiment.

An exterior of the smartphone 1 according to the present embodiment will be described with reference to FIGS. 1 to 3.

A housing 20 includes a front face 1A, a back face 1B, and side faces 1C1 to 1C4. The front face 1A constitutes a front side of the housing 20. The back face 1B constitutes a rear side of the housing 20. The side faces 1C1 to 1C4 each constitutes a lateral side coupling the front face 1A and the back face 1B. Hereinafter, the side face 1C1 to 1C4 may be collectively referred to as side faces 1C without specifying which of the faces are being referred to.

The smartphone 1 includes, on the front face 1A, a touchscreen display 2, buttons 3A to 3C, an illuminance sensor 4, a proximity sensor 5, a receiver 7, a microphone 8, and a camera 12. The smartphone 1 includes a camera 13 on the back face 1B. The smartphone 1 includes buttons 3D to 3F and a connector 14 on the side faces 1C. Hereinafter, the buttons 3A to 3F may be collectively referred to as buttons 3 without specifying which of the faces are being referred to.

The touchscreen display 2 includes a display 2A and a touchscreen 2B. The display 2A includes a display device such as a liquid crystal display (LCD), an organic Electro-Luminescence (EL) panel, or an inorganic Electro-Luminescence (EL) panel. The display 2A displays characters, images, symbols, shapes, etc.

The touchscreen 2B detects a contact on the touchscreen 2B made by a finger or a stylus pen. The touchscreen 2B may detect a position of the contact on the touchscreen 2B made by a plurality of fingers or stylus pens.

The touchscreen 2B may employ any type of a detection method such as a capacitive type, a resistive type, a surface acoustic wave type (or a ultrasonic type), an infrared type, an electromagnetic induction type, or a load detection type. The capacitive type method is capable of detecting contact and approach made by the finger or the styles pen.

Figure 4:
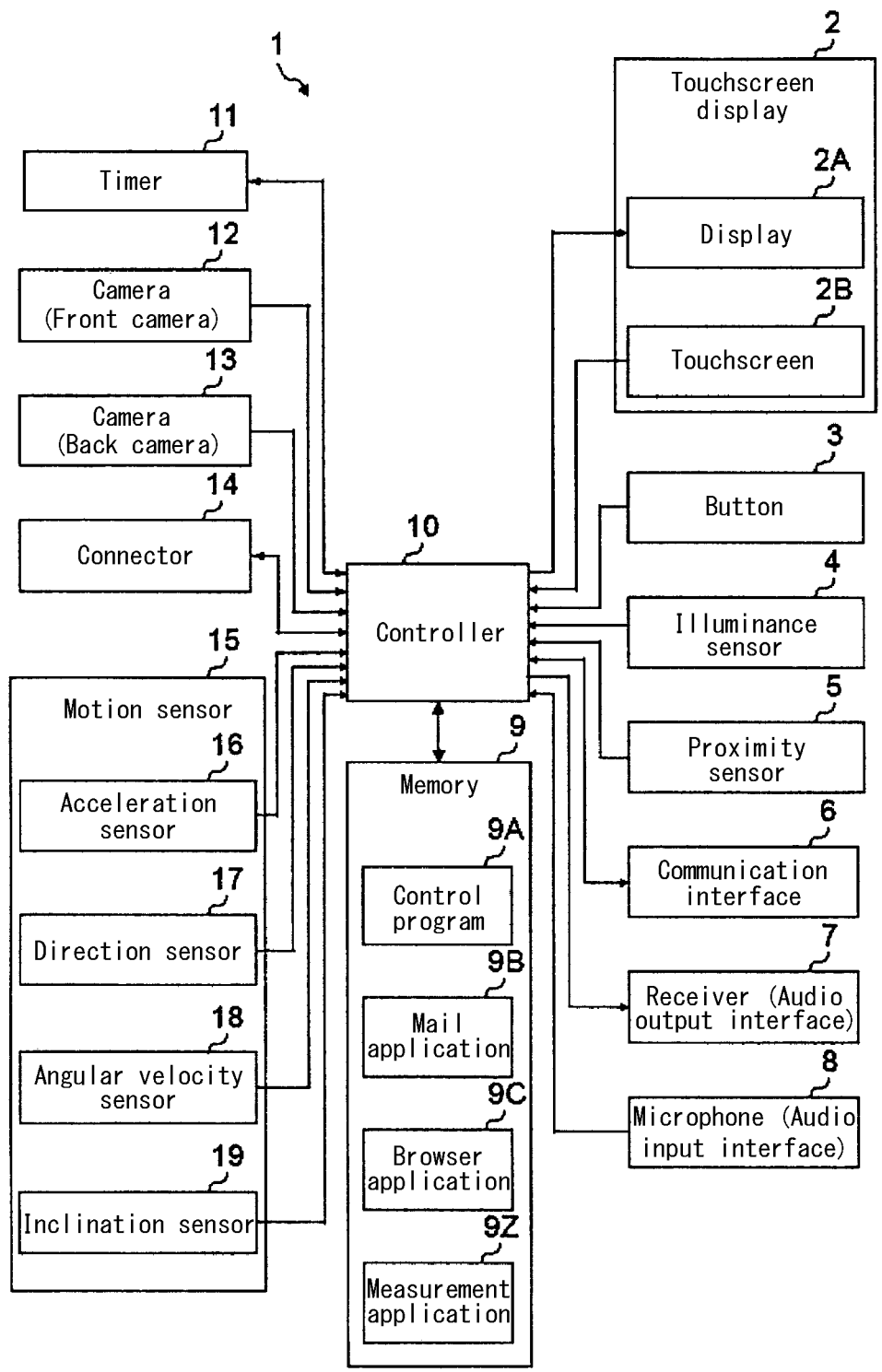
FIG. 4 is a block diagram schematically illustrating functions of the smartphone according to the embodiment.

FIG. 4 is a block diagram illustrating a configuration of the smartphone 1. The smartphone 1 includes the touchscreen display 2, the buttons 3, the illuminance sensor 4, the proximity sensor 5, a communication interface 6, the receiver 7, the microphone 8, a storage (a memory) 9, the controller 10, a timer 11, cameras 12 and 13, a connector 14, and a motion sensor (a measuring unit) 15.

As described above, the touchscreen display 2 includes the display 2A and the touchscreen 2B. The display 2A displays characters, images, symbols, shapes, etc. The touchscreen 2B receives a contact in a reception area as an input. That is, the touchscreen 2B detects the contact. The controller 10 detects a gesture in respect of the smartphone 1. The controller 10 cooperates with the touchscreen 2B and thus detects an operation (a gesture) in respect of the touchscreen 2B (the touchscreen display 2). The controller 10 cooperates with the touchscreen 2B and thus detects an operation (a gesture) in respect of the display 2A (the touchscreen display 2).

The buttons 3 are operated by the user. The buttons 3 include the buttons 3A to 3F. The controller 10 cooperates with the buttons 3 and thus detects an operation in respect of the buttons 3. The operation in respect of the buttons 3 may be, for example, a click, a double click, a push, a long push, and a multi-push.

For example, the buttons 3A to 3C are a home button, a back button, and a menu button, respectively. According to the present embodiment, the buttons 3A to 3C are of a touch sensor type. For example, the button 3D is a power on/off button for the smartphone 1. The button 3D may also serve as a sleep/wake button. For example, the buttons 3E and 3F are volume buttons.

The illuminance sensor 4 detects brightness. For example, the brightness refers to an intensity of light, brightness, luminance, etc. The illuminance sensor 4 is used for, for example, adjusting the brightness of the display 2A.

The proximity sensor 5 detects presence of a nearby object without contact. The proximity sensor 5 detects, for example, the approach of a face to the touchscreen display 2.

The communication interface 6 performs wireless communication. The communication method employed by the communication interface 6 conforms to a wireless communication standard. The wireless communication standard includes, for example, the 2G, 3G, and 4G communication standards for cellular phones. The communication standards for cellular phones include, for example, LTE (Long Term Evolution), W-CDMA (Wideband Code Division Multiple Access), CDMA2000, PDC (Personal Digital Cellular), GSM® (Global System for Mobile communications, GSM is a registered trademark in Japan, other countries, or both), PHS (Personal Handy-phone System), etc. The wireless communication standards include, for example, WiMAX (Worldwide Interoperability for Microwave Access), IEEE802.11, Bluetooth® (Bluetooth is a registered trademark in Japan, other countries, or both), IrDA (Infrared Data Association), NFC (Near Field Communication), etc. The communication interface 6 may support one or more of the communication standards mentioned above.

The receiver 7 outputs an audio signal transmitted from the controller 10 as a voice. The microphone 8 converts the voice of the user into an audio signal and transmits the audio signal to the controller 10. The smartphone 1 may include a speaker in place of the receiver 7.

The storage 9 serves as a memory for storing programs and data. The storage 9 is also used as a memory for provisionally storing the results of processing by the controller 10. The storage 9 may include any storage device such as a semiconductor memory device or a magnetic storage device. The storage 9 may include a plurality of types of storage device. The storage 9 may include a combination of a portable storage medium such as a memory card and a reader for the storage medium.

The programs stored in the storage 9 include applications to be run in the foreground or background, and control programs for assisting operation of the applications. For example, an application causes the display 2A to display a predetermined screen and causes the controller 10 to perform processing corresponding to a gesture detected via the touchscreen 2B. The control program is, for example, an OS (Operating System). The applications and the control programs may be installed in the storage 9 via wireless communication performed by the communication interface 6 or a storage medium.

The storage 9 stores, for example, a control program 9A, a mail application 9B, a browser application 9C, and a measurement application 9Z. The mail application 9B performs mail functions including composing, transmitting, receiving, and displaying mail. The browser application 9C performs Web browsing function for displaying Web pages. The measurement application 9Z performs functions which allow a user to measure an outline of a cross-section (abdomen) of the object with the smartphone 1.

The control program 9A provides functionality relating to various controls for operating the smartphone 1. The control program 9A controls, for example, the communication interface 6, the receiver 7, and the microphone 8 to implement telephone calls. The functionalities of the control program 9A may be used in combination with other functionalities provided by other programs such as the mail application 9B.

The storage 9 stores a visceral fat area estimation formula and a subcutaneous fat area estimation formula which are generated in advance. The storage 9 stores a plurality of cross-sectional abdominal images. These cross-sectional abdominal images are classified based on a combination of the visceral fat area and the subcutaneous fat area.

The controller 10 is, for example, a CPU (Central Processing Unit). The controller 10 may be an integrated circuit such as a SoC with another component such as the communication interface 6 integrated thereinto (System-on-a-Chip). The controller 10 may include a plurality of integrated circuits. The controller 10 implements various functions by centrally controlling operation of the smartphone 1.

In particular, the controller 10 refers to data stored in the storage 9 as necessary. The controller 10 executes instructions stored in the storage 9 and implements various functions by controlling the display 2A, the communication interface 6, or the motion sensor 15. The controller 10 implements various functions by executing instructions included in the measurement application 9Z stored in the storage 9. The controller 10 may perform different control depending on a detection result of each detection unit such as the touchscreen 2B, the buttons 3, and the motion sensor 15. According to the present embodiment, the entire controller 10 functions as a control unit. The controller 10 calculates an outline of a cross-section of an object based on the direction information acquired by the first sensor and the motion information acquired by the second sensor.

Further, the controller 10 calculates a portion of the outline of the cross-section of the object and extracts a characteristic coefficient of the outline. The controller 10 retrieves the visceral fat area estimation formula and the subcutaneous fat area estimation formula stored in the storage 9 and estimates the visceral fat area and the subcutaneous fat area from the characteristic coefficient of the extracted outline. Furthermore, the controller 10 selects one image among a plurality of cross-sectional abdominal images stored in the storage 9, corrects the selected cross-sectional abdominal image based on the calculated outline, and then displays a corrected image on the display 2A.

According to the present embodiment, an example in which the smartphone 1 operates using the storage 9 and the controller 10 will be described. However, the present disclosure is not limited thereto. For example, one or all of the operations described in the present embodiment may be performed by using a memory and a controller which are included in a server connected to a network.

The timer 11 outputs a clock signal of a predetermined frequency. Upon receiving an instruction for operation from the controller 10, the timer 11 outputs the clock signal to the controller 10. The first sensor and the second sensor acquire the direction information and the motion information, respectively, a plurality of times in accordance with the clock signal input via the controller 10. The timer 11 may be provided either internally or externally of the controller 10.

The camera 12 is a front camera for capturing an object facing the front face 1A. The camera 13 is a back camera for capturing an object facing the back face 1B.

The connector 14 is a terminal to which another device is coupled. The connector 14 according to the present embodiment also serves as a communication interface for allowing the smartphone 1 to communicate with another apparatus via a connection object connected to the terminal. The connector may be a general-purpose terminal such as USB (Universal Serial Bus), HDMI® (High-Definition Multimedia Interface, HDMI is a registered trademark in Japan, other countries, or both), MHL (Mobile High-definition Link), Light Peak, Thunderbolt, a LAN connector (Local Area Network connector), or an earphone-microphone connector. The connector 14 may be a specialized terminal such as a Dock connector. An apparatus coupled to the connector 14 may be, for example, a charger, an external storage, a speaker, a communication device, or an information processing apparatus.

The motion sensor 15 detects a motion factor. The motion factor is processed primarily as a control factor of the smartphone 1. The control factor is a factor indicating a status of the smartphone 1 and is processed by the controller 10. The motion sensor 15 according to the present embodiment includes an acceleration sensor 16, a direction sensor 17, an angular velocity sensor 18, and an inclination sensor 19. Outputs from the acceleration sensor 16, the direction sensor 17, the angular velocity sensor 18, and the inclination sensor 19 can be used in combination. By using the outputs from the motion sensor 15 in combination, the controller 10 is able to perform processing which highly reflects the motion of the smartphone 1.

According to the present embodiment, the first sensor acquires the direction information of the smartphone 1. The direction information of the smartphone 1 is information output from the first sensor. The direction information of the smartphone 1 is information concerning a direction in which the smartphone 1 is directed. The direction information of the smartphone 1 includes, for example, a geomagnetic direction, an inclination with respect to the geomagnetic direction, a direction of an angle of rotation, a change in the angle of rotation, a direction of gravity, and an inclination with respect to the direction of gravity.

The direction of the smartphone 1 indicates a normal of a surface of the housing 20 facing an object when measuring an outline of a cross-section of the object. The surface of the housing 20 to face the object may be any surface whose direction can be detected by the first sensor and may be any one of the front face 1A, the back face 1B, and the side faces 1C1 to 1C4.

According to the present embodiment, the direction sensor 17 is used as the first sensor. The direction sensor 17 is a sensor for detecting the geomagnetic direction. According to the present embodiment, the direction information acquired by the direction sensor 17 is a component resulting from projecting a direction of the smartphone 1 onto a plane parallel to the floor. The direction information acquired by the direction sensor 17 indicates the direction of the smartphone 1. The direction of the smartphone 1 can be acquired as direction information indicating 0 to 360 degrees. For example, the direction information indicates 0 degrees when the smartphone 1 is directed to north, 90 degrees when the smartphone 1 is directed to east, 180 degrees when the smartphone 1 is directed to south, and 270 degrees when the smartphone 1 is directed to west. According to the present embodiment, when a cross-section of a measurement object is parallel to the floor, the direction sensor 17 may acquire the direction information more accurately. According to the present embodiment, the object is a human abdomen, and the person may be measured in a standing-up state.

The direction sensor 17 outputs a detected geomagnetic direction. For example, when the geomagnetic direction is output as the motion factor, the controller 10 may use it as a control factor reflecting the direction of the smartphone 1. For example, when a change in the geomagnetic direction is output as the motion factor, the controller 10 may use it as a control factor reflecting the change in the direction of the smartphone 1.

The angular velocity sensor 18 may be used as the first sensor. The angular velocity sensor 18 detects an angular velocity of the smartphone 1. The angular velocity sensor 18 may acquire the angular velocity of the smartphone 1 as the direction information. The controller 10 calculates the direction of the smartphone 1 by performing time-integration of the angular velocity. The calculated direction of the smartphone 1 corresponds to a relative angle with reference to an initial value of the measurement.

The angular velocity sensor 18 outputs the detected angular velocity. For example, when a direction of the angular velocity is output as the motion factor, the controller 10 may use it as a control factor reflecting a rotation direction of the smartphone 1. For example, when a magnitude of the angular velocity is output, the controller 10 may use it as a control factor reflecting a rotation amount of the smartphone 1.

The inclination sensor 19 may be used as the first sensor. The inclination sensor 19 detects a gravitational acceleration acting on the smartphone 1. The inclination sensor 19 may acquire the gravitational acceleration of the smartphone 1 as the direction information. For example, the smartphone 1 may acquire direction information indicating −9.8 to 9.8 m/sec$^2$ from the inclination sensor 19. For example, when a y-axis direction of the smartphone 1 illustrated in FIG. 1 coincides with the direction of gravity of the smartphone 1, the direction information indicating 9.8 m/sec$^2$ is acquired. When the y-axis direction of the smartphone 1 is opposite to the direction of gravity, direction information indicating −9.8 m/sec$^2$ is acquired. Further, when the y-axis direction is orthogonal to the direction of gravity, direction information indicating 0 m/sec$^2$ is acquired.

The inclination sensor 19 outputs the detected inclination. For example, when the inclination with respect to the direction of gravity is outputted as the motion factor, the controller 10 may use it as a control factor reflecting the inclination of the smartphone 1.

The controller 10 may calculate the direction using the direction information of the smartphone 1. For example, the angular velocity sensor 18 described above acquires the angular velocity as the direction information. The controller 10 calculates the direction of the smartphone 1 based on the angular velocity. For example, the inclination sensor 19 described above acquires the gravitational acceleration as the direction information. The controller 10 calculates the direction of the smartphone 1 with respect to the direction of gravity based on the gravitational acceleration.

The first sensor may use a combination of the motion sensors described above. By processing direction information from a plurality of motion sensors, the controller 10 may calculate the direction of the smartphone 1 more accurately.

According to the present embodiment, the second sensor serves as a device for acquiring the motion information of the respective apparatus. The second sensor acquires the motion information of the smartphone 1. The motion information is output from the second sensor. The motion information of the smartphone 1 corresponds to displacement of the smartphone 1. The motion information of the smartphone 1 includes, for example, acceleration, speed, and the displacement.

According to the present embodiment, the displacement of the smartphone 1 corresponds to the displacement of a reference position on the housing 20 of the smartphone 1. The reference position on the housing 20 may be in any position that can be detected by the second sensor and may be, for example, the surface of the side face 1C1.

According to the present embodiment, the acceleration sensor 16 is used as the second sensor. The acceleration sensor 16 detects acceleration acting on the smartphone 1. The acceleration sensor 16 may acquire the acceleration of the smartphone 1 as the motion information. The controller 10 calculates the displacement of the smartphone 1 by performing double time integration of the acquired acceleration.

The acceleration sensor 16 outputs the detected acceleration. For example, when the direction of the acceleration is output, the controller 10 may use it as the control factor reflecting the moving direction of the smartphone 1 for the processing. For example, when the magnitude of the acceleration is output, the controller 10 may use it as a control factor reflecting the moving speed and the displacement of the smartphone 1 for the processing.

The controller 10 calculates the outline of the cross-section of the object. The outline of the cross-section of the object is calculated based on the direction information acquired by the first sensor and the motion information acquired by the second sensor. The controller 10 may calculate the direction and the displacement in the course of the calculation.

Each of the motion sensors 15 described above includes a sensor capable of detecting the motion factor in three axial directions. The three axial directions detected by the motion sensor 15 according to the present embodiment are substantially orthogonal to one another. An x-direction, a y-direction, and a z-direction illustrated in FIGS. 1 to 3 correspond to the three axial directions of the motion sensor 15. The three axial directions do not need to be orthogonal to one another. The motion sensor 15 in which the three directions are not orthogonal to one another may calculate the motion factor in the three directions orthogonal to one another. Each of the motion sensors 15 may have a different reference direction. According to the present embodiment, each motion sensor does not need to detect three axial directions. The controller 10 may calculate an outline of a cross-section based on direction information about one axial direction and motion information about one axial direction.

The first sensor and the second sensor are included in the measuring unit for measuring an outline of a cross section. The first sensor and the second sensor may be implemented by any one of the motion sensors 15 described above, or other motion sensors.

Some or all of the programs and data stored in the storage 9 in FIG. 4 may be downloaded from another device through wireless communication performed by the communication interface 6. Some or all of the programs stored in the storage 9 in FIG. 4 may be stored in a storage medium that may be read by the reader in the storage 9. Some or all of the programs stored in the storage 9 in FIG. 4 may be stored in a storage medium that may be read by a reader coupled to the connector 14. The storage medium may be, for example, a flash memory, HDD® (Hard Disc Drive, HDD is a registered trademark in Japan, other countries, or both), CD (Compact Disc), DVD (Digital Versatile Disc, DVD® is a registered trademark in Japan, other countries, or both), or BD (Blu-ray® Disc, Blue-ray is a registered trademark in Japan, other countries, or both).

The configuration of the smartphone 1 is illustrated in FIGS. 1 to 4 by way of example, and may be altered as appropriate within a range that does not impair the gist of the present disclosure. For example, the number and type of the buttons 3 is not limited to the example of FIG. 1. For example, the smartphone 1 may include buttons in a numeric keypad sequence or buttons having a QWERTY layout as buttons for operation of a screen, in place of the buttons 3A to 3C. The smartphone 1 may have one button for the operation of the screen, or no buttons. Although in the example illustrated in FIG. 4 the smartphone 1 includes two cameras, the smartphone 1 may have one camera or no cameras. The illuminance sensor 4 and the proximity sensor 5 may be integrally implemented by one sensor. Although in the example illustrated in FIG. 4 four sensors are provided to acquire the direction information and the motion information of the smartphone 1, the smartphone 1 may omit some of the sensors or include a different type of a sensor.

Figure 5:
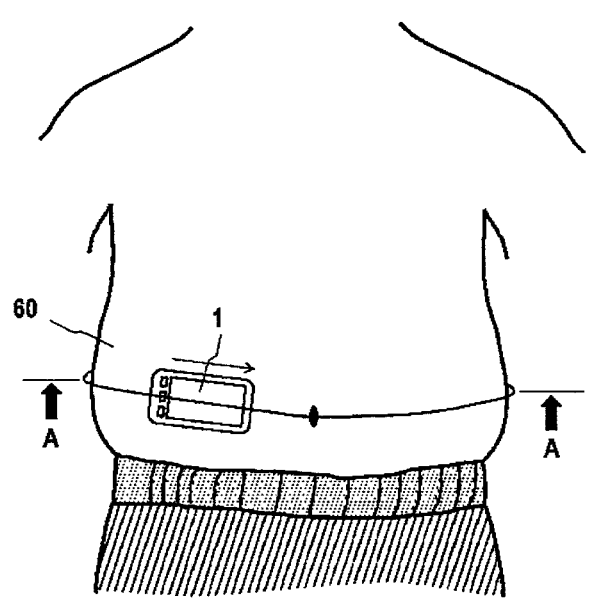
FIG. 5 is a diagram schematically illustrating a measuring state of an outline of an abdomen according to the embodiment.

Next, the measurement of an outline of an abdomen by the smartphone 1 according to the embodiment will be described with reference to FIGS. 5 and 6. FIG. 5 is a diagram schematically illustrating a measuring state of the outline of the abdomen according to the embodiment. FIG.

6 is a flowchart illustrating operation before displaying a cross-sectional abdominal image according to the embodiment. According to the present embodiment, by way of example, the user moves the smartphone 1 along an approximate semicircle of the abdomen between the navel and the spine.

Figure 6:
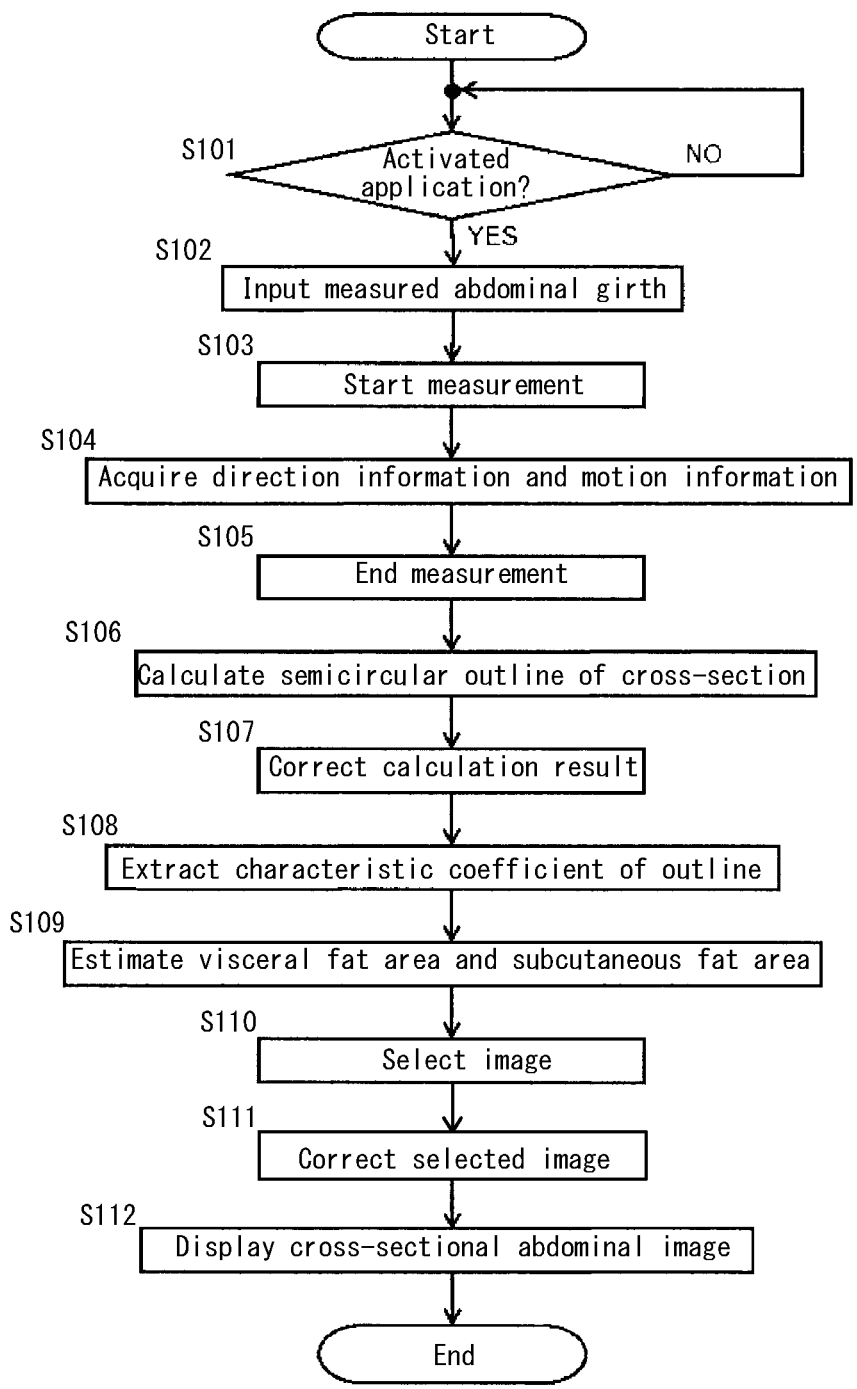
FIG. 6 is a flowchart illustrating an example of operations as far as displaying a cross-sectional abdominal image.

As illustrated in FIG. 6, the user activates the measurement application 9Z for the measurement of the outline of the abdomen in step S101.

After activating the measurement application 9Z, the user inputs the value of the abdominal girth measured in advance using a tape measure or the like to the smartphone 1 (step S102). Alternatively, the smartphone 1 may read the value of the abdominal girth from user information stored in the storage 9 in advance. Step S102 does not necessarily need to be performed before the measurement. Step S102 may be performed after the measurement ends in step S105.

In step S103, next, the user starts the measurement using the smartphone 1. The user performs the measurement in the upright state. At the start of the measurement, the smartphone 1 is positioned on the navel and in contact with the surface of the abdomen 60. A measurement start position is selected as appropriate depending on the portion of the abdominal cross-section to be calculated. According to the present embodiment, the outline of the user's abdomen at the height of the naval is measured as indicated by the line A-A in FIG. 5. When the measurement start position is preset to the naval or the like, a range of the outline to be calculated is fixed for each user, thus reducing errors in the characteristic coefficients of the outline, which will be described later. The user starts the measurement while placing the smartphone 1 on, for example, the naval. The user starts the measurement by performing a start action preset to the smartphone 1. The preset start action may be pressing any one of the buttons 3 of the smartphone 1, or tapping a particular location on the touchscreen 2B. The face of the smartphone 1 to be brought into contact with the surface of the abdomen may be any one of the front face 1A, the back face 1B, and the side faces 1C1 to 1C4. In FIG. 5, the back face 1B is brought into contact, for better operability.

In step S104, the user moves the smartphone 1 along the line A-A on the surface of the abdomen 60. Here, the smartphone 1 may be moved at a constant speed while maintaining contact with the surface of the abdomen 60. Thus, information may be acquired at constant intervals, improving the accuracy of the measurement of the outline.

In step S104, under a preprogrammed condition, the smartphone 1 acquires the angular velocity (degrees/sec) as the directional information from the angular velocity sensor 18 and the motion information from the acceleration sensor 16. The direction information is acquired a plurality of times in accordance with the clock signal output from the timer 11. A cycle for acquiring each information is appropriately determined based on a size and/or complexity of the cross-section of the measured object. The cycle for acquiring the information is appropriately selected from, for example, a sampling frequencies 5 to 60 Hz. The direction information acquired in accordance with the clock signal is stored in the smartphone 1 together with information about acquisition times. This measurement is continuously executed from the start in step S103 to the end in step S105.

The user moves the smartphone 1 around at least the semicircle of the abdomen at a constant speed while keeping the smartphone 1 in contact with the surface of the abdomen 60. According to the present embodiment, the semicircle corresponds to a part between the navel and the center of the back. The motion along the semicircle of the abdomen provides sufficient information for the calculation of the outline and enables the calculation of the characteristic coefficient, which will be described later. The smartphone 1 may be equipped with a means for notifying the user that the smartphone 1 has been moved around the semicircle of the abdomen.

After moving the smartphone 1 by at least the semicircle of the abdomen, the user performs a preset ending action to the smartphone 1 and thus ends the measurement (step S105). The preset ending action may be pressing any one of the buttons 3 of the smartphone 1 or tapping a particular location on the touchscreen 2B. Alternatively, when step S106 described later is simultaneously performed, the smartphone 1 may autonomously end the measurement by determining that the smartphone 1 has been moved around the semicircle of the abdomen, at a point when the direction of the smartphone 1 changes by a 180 degrees from the start of the measurement. This eliminates the necessity for the user to perform the ending action, and thus measurement is simplified.

After or during the measurement, the controller 10 calculates a semicircular outline of the abdomen (step S106). The controller 10 calculates the direction of the smartphone 1 by integrating the angular velocity acquired in step S104.

Figures 7, 8:
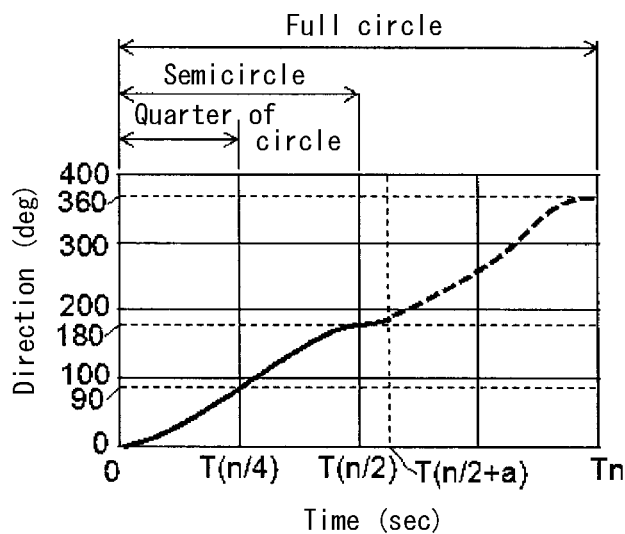
FIG. 7 is a graph illustrating an example of directions of the smartphone according to the embodiment.
FIG. 8 is a diagram illustrating an example of records generated based on acquired information according to the embodiment.

FIG. 7 illustrates an example of the direction of the smartphone 1 according to the present embodiment. A method for extracting information about the semicircle of the abdomen from the acquired direction information will be described with reference to FIG. 7. In FIG. 7, the transverse axis represents time. The measurement starts at 0 seconds, and the measurement end at T (n/2+a) seconds. Here, n represents 360 degrees as one circle of the abdomen, and a represents an angle obtained by subtracting 180 degrees corresponding to the semicircle of the abdomen from a direction at the end of the measurement. The vertical axis represents the direction of the smartphone 1. In the figure, the solid line represents acquired information, and the dotted line represents a virtual line corresponding to information about the remaining portion of the abdomen, which is not acquired. A flat portion in the vicinity of the direction of 180 degrees is estimated as information about the back. It is judged that the center of the back was passed based on the center of the flat portion, and the semi-circular portion is determined. That is, the information between 0 seconds and T(n/2) seconds in the figure is extracted as the information about the semicircle of the abdomen. This is an example of the method for extracting the information about the semicircle of the abdomen. For example, when the flat portion deviates from the 180 degree position, the flat portion may be normalized to correspond to 180 degrees. Information about a position corresponding to −180 degrees from the flat portion may be normalized to the start position. Or, information about a position with the smallest curve in the vicinity of the 180 degree position may be determined as corresponding to the center of the back, in place of the information about the center of the flat portion.

FIG. 8 illustrates examples of records including acquired and normalized information according to the present embodiment. Record R0 corresponds to the start point (the position of the naval according to the present embodiment) of the extracted semicircular outline, and record R(n/s) corresponds to the end point (the center of the back according to the present embodiment, corresponding to 180 degrees) of the semicircle. Record R(n/2+a) corresponds to the acquired final information. Each record includes a combination of the direction information and the motion information. The motion information corresponds to the displacement estimated based on a record number (or time) representing clock information. According to the present embodiment, the records for directions at 0 to 180 degrees are extracted as the information about the semicircle. In the motion information of the record R(n/2+a), a value corresponding to half the measured value of the user's abdominal girth is stored. Each record is acquired at constant intervals. The smartphone 1 is assumed to be moving at a constant speed. Thus, the intervals of the displacement for the motion information are constant. The records thus acquired are displayed as a diagram illustrating the semicircular outline of the abdomen. When the records R0 to R(n/2) are plotted on XY coordinates in an appropriate order based on the direction and the displacement, the semicircle of the cross-section of the object may be calculated. Note that step S106 may be performed simultaneously with step S104.

In step S107, the smartphone 1 corrects the result calculated in step S106. The smartphone 1 calculates the outline of the user's abdomen by correcting the calculated result in step S107. This correction is a preprocessing for the extraction of the characteristic coefficient of the outline executed in subsequent step S108. The characteristic coefficient of the outline changes in accordance with the direction of the outline at any XY coordinate and position of the outline. According to the present embodiment, the direction of the outline corresponds to the direction of the axis of symmetry, which will be described later, and the position on the outline corresponds to the position of the center, which will be described later. The correction of the direction and the position of the outline may reduce variations in the characteristic coefficients of the outline caused by different measurement conditions. The correction of the direction and the position of the outline may be readily performed by correcting the calculated semicircular outline of the abdomen based on an inverted closed curve folded with an axis of symmetry connecting a start point (the position of the navel according to the present embodiment) and an end point (the center of the back according to the present embodiment). In order to correct the direction of the outline, the inverted closed curve is turned such that the axis of symmetry of the inverted closed curve (a line connecting the navel and the center of the back) is directed in a particular direction. In order to correct the position of the outline, the inverted closed curve is moved such that the center thereof meets the origin of the coordinate system. The correction of the direction and the position may be performed according to known techniques.

Figures 9, 10:
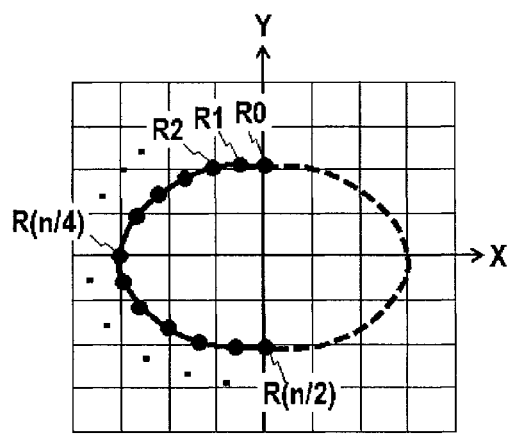
FIG. 9 is a diagram illustrating an outline of an abdomen calculated and corrected according to the embodiment.
FIG. 10 is a diagram illustrating an example of a classification table of a cross-sectional abdominal image according to the embodiment.

FIG. 9 is a diagram illustrating an outline of the abdomen calculated and corrected according to the present embodiment. The solid line in the figure is a calculated semicircular outline of the abdomen. The dotted line in the figure represents a virtual curve obtained by flipping the calculated semicircular outline of the abdomen. The black dots represent acquired records plotted on the XY coordinates.

After correcting the calculated result in step S107, the smartphone 1 extracts the characteristic coefficients of the semicircular outline of the abdomen (step S108). Methods for extracting the characteristic features of a shape of the curve include methods for calculating a curvature function. According to the present embodiment, however, a method using Fourier analysis will be described. A Fourier coefficient may be acquired by performing Fourier analysis on the curve of the semicircular outline of the abdomen or the inverted closed curve. As is well known, the Fourier coefficient of each order obtained by performing the Fourier analysis on the curve is used as a coefficient indicating characteristics of a shape. The order of the Fourier coefficient used as the characteristic coefficient is determined at the time of generation of each estimation formula, as will be described in detail later. According to the present embodiment, Fourier coefficients $Sa_1$, $Sa_2$, $Sa_3$, and $Sa_4$ concerning the visceral fat area are extracted as characteristic coefficients of the visceral fat. Fourier coefficients $Sa_1$, $Sa_2$, $Sa_3$, and $Sa_4$ concerning the subcutaneous fat area are extracted as characteristic coefficients of the subcutaneous fat. When an independent variable is a main component of the estimation formula at the time of generation of each estimation formula, the main component may be extracted as the characteristic coefficient.

The smartphone 1 estimates a visceral fat area A and a subcutaneous fat area B of the user by substituting the visceral fat area estimation formula and the subcutaneous fat area estimation formula acquired in advance with the characteristic coefficients $Sa_1$ to $Sa_4$ and $Sb_1$ to $Sb_4$ extracted in step S108 (step S109). An example of the visceral fat area estimation formula and an example of the subcutaneous fat area estimation formula are expressed as formula 1 and formula 2, respectively.

$$A = -483.8 + 46.2 \times Sa_1 - 13.6 \times Sa_2 + 36.8 \times Sa_2 + 43.2 \times Sa_1 \quad \text{[Formula 1]}$$

$$B = -280.0 + 41.6 \times Sb_1 - 24.9 \times Sb_2 + 16.6 \times Sb_2 - 40.0 \times Sb_2. \quad \text{[Formula 2]}$$

The formulas 1 and 2 are calculated based on a correlation between the outline (shape) of the abdomen measured when the user is in the upright state and a CT image acquired when the user is in the recumbent state. Thus, the visceral fat area A and the subcutaneous fat area B estimated in step S109 correspond to the visceral fat area A and the subcutaneous fat area B, respectively, acquired by measuring the user in the recumbent state. Methods for generating the visceral fat area estimation formula and the subcutaneous fat area estimation formula will be described in detail later.

Subsequently, the smartphone 1 selects an image most similar to the user's abdominal cross-section based on the visceral fat area A and the subcutaneous fat area B estimated in step S109 (step S110).

FIG. 10 illustrates an example of a classification table of the cross-sectional abdominal image according to the present embodiment. The smartphone 1 stores the classification table illustrated in FIG. 10 in the storage 9 in advance. According to the present embodiment, the smartphone 1 stores 25 images (P11 to P55) with different ranges of visceral fat area and subcutaneous fat area. The 25 images may be CT images of the abdomen, schematic images thereof, or marks. The image corresponding to the estimated visceral fat area A and the estimated subcutaneous fat area B of the user is selected from the 25 images. For the selection of the image, the smartphone 1 may utilize various information such as the user's age, input in advance by the user.

Next, the smartphone 1 corrects the image selected in step S110 based on the outline of the user's abdomen calculated in step S107 (step S111). The smartphone 1 corrects the selected cross-sectional abdominal image based on, for example, an aspect ratio of the calculated outline of the abdomen. That is, the smartphone 1 corrects the image such that the aspect ratio of the cross-sectional abdominal image matches the aspect ratio of the calculated outline of the abdomen. The smartphone 1 may correct the cross-sectional abdominal image such that, for example, a shape of the outline in the cross-sectional abdominal image matches a shape of the calculated outline of the abdomen.

The image corrected in step S111 is displayed on the display 2A of the smartphone 1 (step S112).

Figure 11:
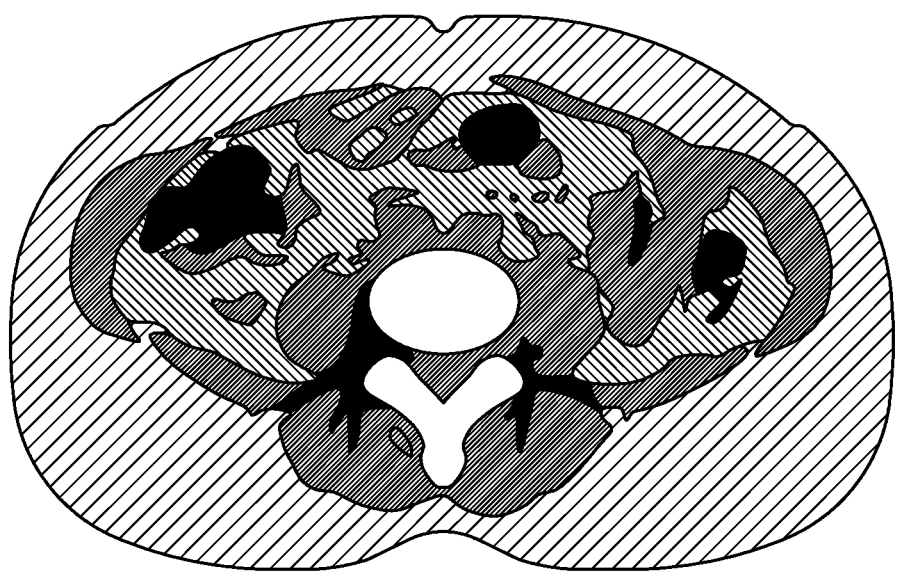
FIG. 11 is a diagram illustrating an example of a selected cross-sectional abdominal image according to the embodiment.
Figure 12:
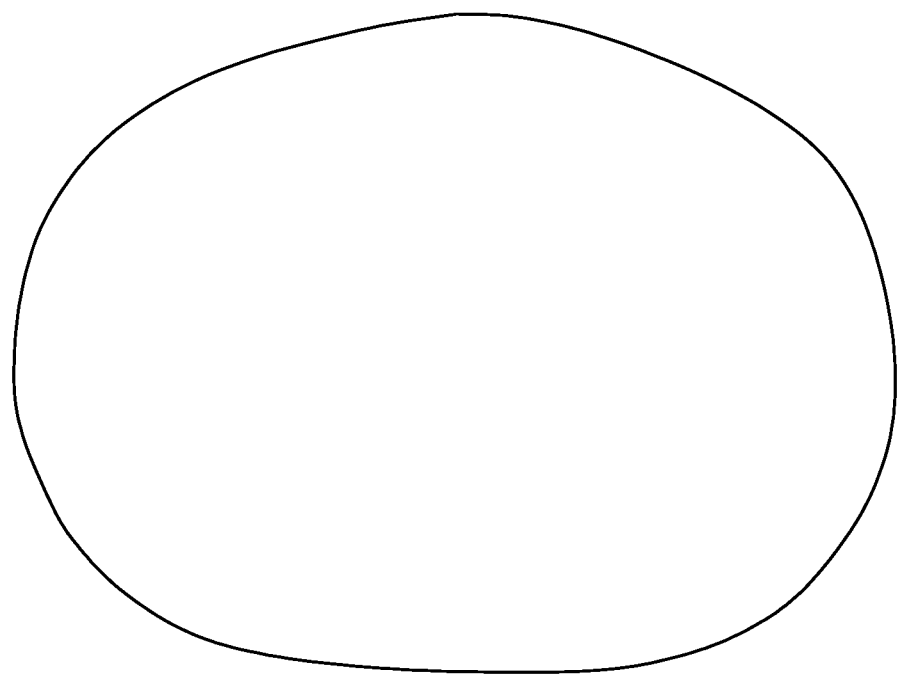
FIG. 12 is a diagram illustrating an example of a calculated outline of an abdomen according to the embodiment.
Figure 13:
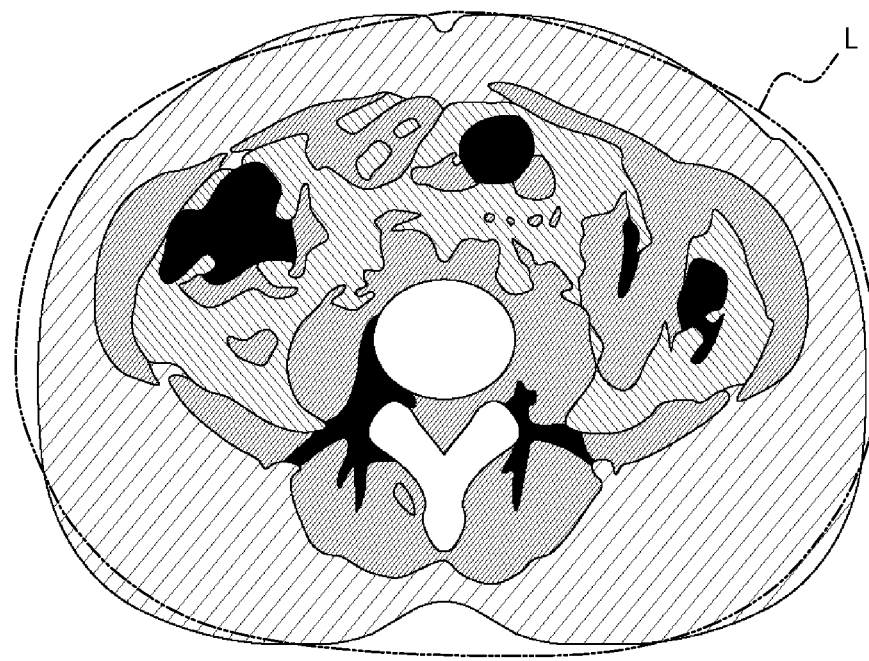
FIG. 13 is a diagram illustrating an example of correction of the cross-sectional abdominal image according to the embodiment.

Here, the correction of the cross-sectional abdominal image performed by the smartphone 1 will be further described with reference to FIGS. 11 to 13. FIG. 11 is a diagram illustrating an example of the cross-sectional abdominal image selected in step S110. The cross-sectional abdominal image illustrated in FIG. 11 is acquired by measuring the user in the recumbent state. FIG. 12 is a diagram illustrating an example of the outline of the abdomen calculated in step S108. The outline of the abdomen illustrated in FIG. 12 is acquired by measuring the user in the upright state.

The smartphone 1 corrects the cross-sectional abdominal image illustrated in FIG. 11 based on the outline of the abdomen illustrated in FIG. 12 in step S111. FIG. 13 is a diagram illustrating an example of the correction in step S111. As illustrated in FIG. 13, the correction causes the outline in the cross-sectional abdominal image to approximate to the shape of the outline of the abdomen in FIG. 12. The smartphone 1 displays an area between the cross-sectional abdominal image in which the outline is corrected and the outline L of the abdomen as the subcutaneous fat. The smartphone 1 omits a region in the cross-sectional abdominal image in which the outline is corrected and outside the outline L of the abdomen. That is, this region is not displayed on the smartphone 1. In this way, the smartphone 1 corrects the outline in the cross-sectional abdominal image by causing the outline to approximate to the outline of the abdomen. In the cross-sectional abdominal image, however, it may be difficult to measure a portion at the navel (i.e., an upper recess in the cross-sectional abdominal image of FIG. 13) and a portion at the center of the back (i.e., a lower recess in the cross-sectional abdominal image of FIG. 13) with the smartphone 1. Thus, the smartphone 1 performs correction in such a manner as to match the outline of the abdomen to the cross-sectional abdominal image.

According to the present embodiment, an example in which all of the steps are performed by the smartphone 1 has been described. However, the present disclosure is not limited thereto, and at least a portion of each step may be performed by a server or the like connected via a network. For example, steps S103 to S105 for the measurement and step S112 for display may be performed by the smartphone 1, while other steps may be performed by the server connected via the network. By performing complex calculations on the server, the processing speed from the start to the end can be improved.

Figure 14:
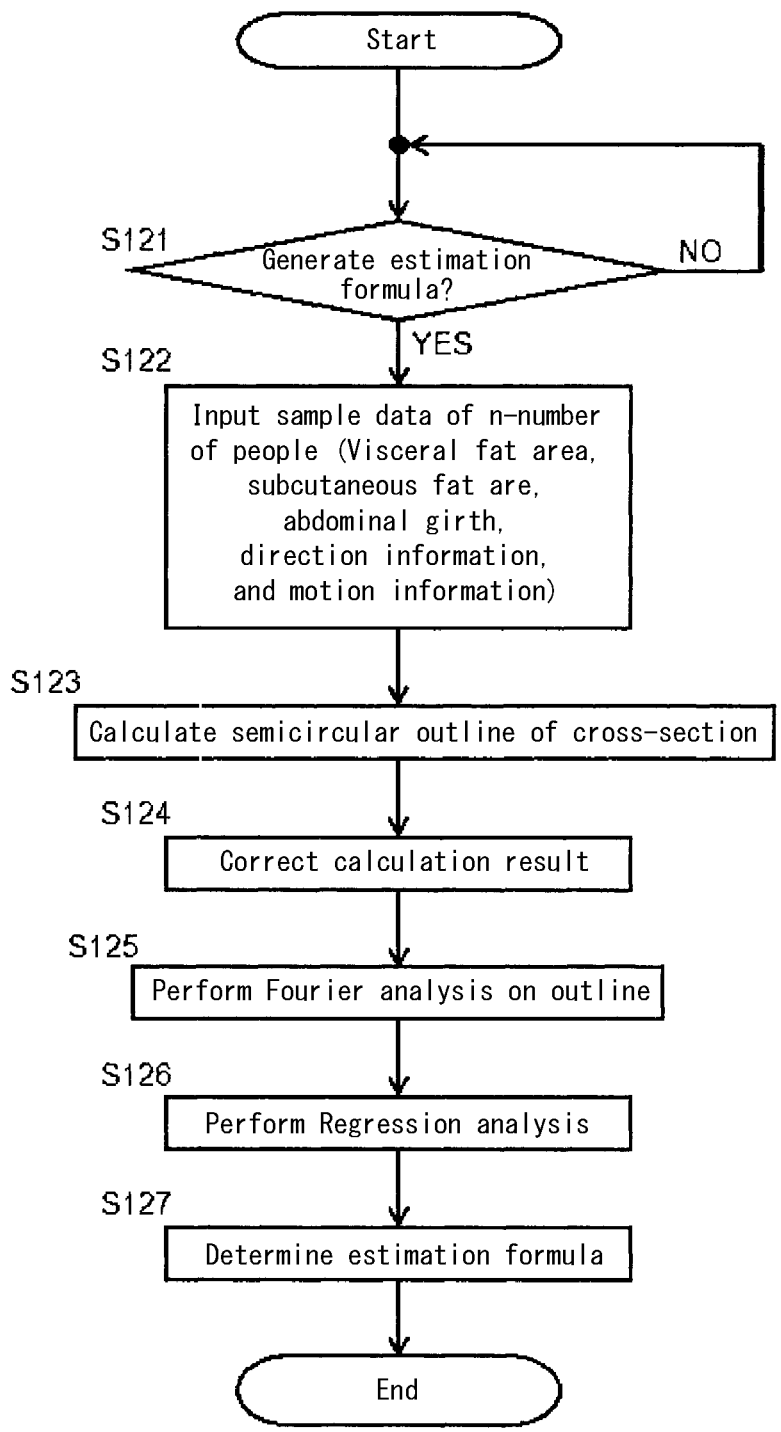
FIG. 14 is a flowchart for generating a visceral fat area estimation formula and a subcutaneous fat area estimation formula according to the embodiment.

FIG. 14 is a flowchart for generating the visceral fat area estimation formula and the subcutaneous fat area estimation formula according to the present embodiment. A procedure for generating the formulas 1 and 2 set forth above will be described with reference to FIG. 14. The smartphone 1 does not need to generate these estimation formulas. The estimation formulas may be calculated in advance by another computer or the like. The estimation formulas thus generated are pre-stored in the application. This eliminates the necessity for the user to generate or change the estimation formulas.

In step S121, an operator performs generation of the estimation formula. In step S122, the operator inputs sample data of a predetermined number of people acquired in advance to the computer. The sample data is data acquired from the predetermined number of sampling subjects. The sample data for one sampling subject includes at least the visceral fat area and the subcutaneous fat area obtained by the CT, the abdominal girth measured with a tape measure or the like, and the direction information and the motion information acquired by the smartphone 1. The visceral fat area and the subcutaneous fat area in the sample data are calculated from data (a CT image) detected when the sampling subject is in the recumbent state. The abdominal girth, the direction information and the motion information in the sample data are detected when the sampling subject is in the upright state. In order to improve the accuracy of the estimation formulas, the predetermined number of sampling subjects may be a sufficient number of people from a statistical viewpoint, and may be a group having a visceral fat distribution similar to those of people would be subject to a diagnosis of metabolic syndrome (hereinafter, simply referred to as "MS").

Subsequently, a computer calculates the semicircular outline of the abdomen by using the abdominal girth, the direction information, and the motion information which have been input (step S123). Also, the computer corrects the semicircular outline of the abdomen thus calculated (step S124). The procedure in step S123 and the procedure in step S124 are similar to the procedure in step S106 and the procedure in step S107, respectively, of FIG. 6 described above, and thus detailed description thereof will be omitted.

Next, the computer performs Fourier analysis on the curve of the corrected semicircular outline of the abdomen or the inverted closed curve (step S125). The computer may acquire a plurality of Fourier coefficients by performing the Fourier analysis on the curve of the outline of the abdomen. As is well known, each of the Fourier coefficients acquired by performing the Fourier analysis on the curve are used as coefficients related to a shape. According to the present embodiment, the computer performs the Fourier analysis on the sample data of a predetermined number of people, and thus acquires Fourier coefficients of the X-axis, the Y-axis, and 1 to k degrees (k is any integer) thereof. The computer may further perform a known principal component analysis to reduce the number of degrees. The principal component analysis is an analytical technique for generating a type of synthetic variable (a principal component) by seeking a component in common with multivariate data (a plurality of Fourier coefficients according to the present embodiment). The principal component analysis enables expression of characteristics of the curve with a fewer number of variables.

Then, the computer performs a regression analysis by using a plurality of Fourier coefficients (or principal components) acquired in step S125 and the visceral fat area input in advance (step S126). The regression analysis is one statistical method for analyzing a relation between a resulting variable and a causing factor and thus discovering the relation. The visceral fat area estimation formula is generated by performing regression analysis on the data of the predetermined number of sampling subjects by using the Fourier coefficient (or the principal component) as an independent variable and the visceral fat area obtained by the CT as a dependent variable. A similar calculation is performed for the subcutaneous fat area, and thus the subcutaneous fat area estimation formula is generated.

Examples of the estimation formulas thus generated are the formulas 1 and 2 set forth above. The independent variables $Sa_1$ to $Sa_4$ of the estimation formula 1 and $Sb_1$ to $Sb_4$ of the estimation formula 2 are characteristic coefficients used for the estimation of the visceral fat area and the subcutaneous fat area of the user. Some or all of the characterized coefficients $Sa_1$ to $Sa_4$ of the visceral fat area estimation formula and the characteristic coefficients $Sb_1$ to $Sb_4$ of the subcutaneous fat area may be the same Fourier coefficients. Thus, the visceral fat area estimation formula and the subcutaneous fat area estimation formula may be generated by employing the statistical means described above (i.e., the principal component analysis and the regression analysis).

In step S126, the estimation formulas are generated by performing the regression analysis on the visceral fat area and the subcutaneous fat area in step S126. By using a similar approach, an estimation formula for the circumference of the abdominal cross-section may be also generated. That is, the computer may perform the regression analysis by using a plurality of Fourier coefficients (or principal components) acquired in step S125 and the abdominal girth input in advance. The computer performs the regression analysis by using the abdominal girth measured by a tape measure or the like as the dependent variable and also using the data of the predetermined number of sampling subjects. Thus, the estimation formula for the circumference of the abdominal cross-section may be generated.

According to the present embodiment, as described above, the smartphone 1 displays an image acquired by correction based on the calculated outline of the user's abdomen. This enables the user to easily recognize that the displayed image is the user's abdominal image and visually recognize a state of the abdominal cross-section. When the smartphone 1 displays the abdominal CT image, the estimated shape of the user's abdominal cross-section may be realistically visualized, which may be effectively used for MS guidance. When the values of the visceral fat area and the subcutaneous fat area are displayed together with the image, the user may recognize detailed accumulation states of the visceral fat and the subcutaneous fat.

According to the present embodiment, the smartphone 1 may measure the semicircular outline of the abdominal cross-section in a simple and accurate manner. Thus, the visceral fat area and the subcutaneous fat area may be accurately and quickly estimated.

As the outline of the human abdominal cross-section is substantially symmetrical, the smartphone 1 according to the present embodiment may estimate the visceral fat area and the subcutaneous fat area of the abdominal cross-section by simply calculating at least the semicircular outline of the cross-section. This enables the user to move the smartphone 1 simply by at least the semicircle of the outline of the abdomen, thus reducing the measurement time. Further, the user does not need to pass the smartphone 1 to the other hand during the measurement. Thus, the user may easily move the smartphone 1 at a constant speed, enhancing the measurement accuracy.

The visceral fat area estimation formula and the subcutaneous fat area estimation formula are calculated based on the correlation between the outline of the abdomen acquired by measuring the user in the upright state and the CT image acquired by measuring the user in the recumbent state. This enables the user to view an estimated CT image by measuring the outline of the abdomen in the upright state without lying in the recumbent state.

Next, a system according to an embodiment will be described in detail with reference to the drawings.

Figure 15:
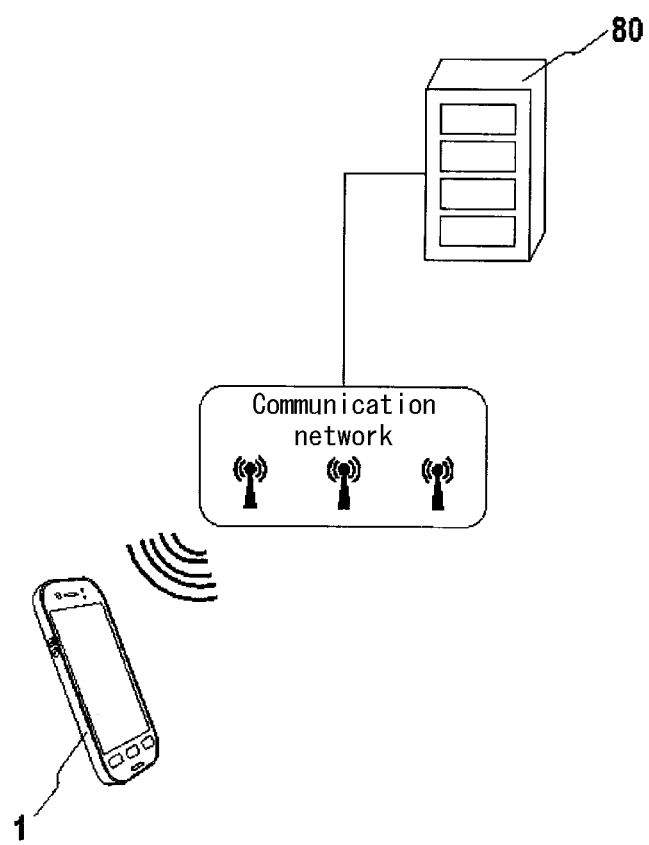
FIG. 15 is a diagram schematically illustrating an apparatus equipped with a communication means, and a system according to an embodiment.

The system according to the present embodiment illustrated in FIG. 15 includes a server 80, the smartphone 1, and the communication network. As illustrated in FIG. 15, the calculation result of the outline of the cross-section measured by the smartphone 1 is transmitted to the server 80 via the communications network. The server 80 classifies and determines the outline of the cross-section and returns an image and advice to the user. The smartphone 1 may display the image and the like transmitted from the server 80 on the display 2A. By utilizing the communication means of the smartphone 1, the server 80 may collect information from a plurality of users, thus further improving accuracy of the classification and determination. In this system, the direction information, the motion information, and the abdominal girth which are acquired may be transmitted to the server 80. In this case, the server 80 calculates the outline of the cross-section, thus reducing a burden imposed on the controller 10 of the smartphone 1 being used by the user. This enables size reduction and simplification of the smartphone 1 and increases the processing speed of the calculation.

Although the system according to the present embodiment includes the smartphone 1 and the server 80 connected to each other via the communication network, the system according to the present disclosure is not limited thereto. The system needs to simply include a measuring instrument to be moved along a surface of an object, a first sensor for acquiring direction information of the measuring instrument, a device for obtaining motion information of the measuring instrument, and a controller configured to calculate an outline of a cross-section of the subject. The measuring instrument, the first sensor, the device, and the controller may be connected to one another via a communication means.

A plurality of embodiments have been described for the purpose of fully and clearly disclosing the present disclosure. However, the appended claims are not limited to the embodiments described above and can implement all modifications and alternative configurations that may be generated by those who are skilled in the art within the scope of the fundamentals shown herein.

In the above embodiments, for example, the smartphone 1 has been described as the apparatus. However, the apparatus according to the present disclosure is not limited thereto, and simply needs to include a measuring instrument equipped with a first sensor and a device, and a controller. Further, the apparatus does not need to include the first sensor, the device and the controller, and these components may be provided separately.

Although in the above embodiments the smartphone 1 is used for the measurement of the outline of the abdominal cross-section, the smartphone 1 may also be used for measurement of an outline of a cross-section of another object.

In the above embodiments, the acceleration sensor is used as the second sensor. However, the second sensor may be anything that is capable of acquiring the motion information of its own device. For example, an electronic tape measure or an electronic roller distance meter configured to acquire the motion information by detecting the number of rotations of a wheel may be used.

In the above embodiments, an example in which the outline of the abdomen is measured by moving the smartphone 1 by at least the semicircle of the abdomen has been described. However, this is not restrictive. For example, by measuring more than the semicircular outline of the abdomen, the accuracy of the measurement is further improved. For example, the smartphone 1 may estimate the fat area by measuring less than the semicircular outline of the abdomen. The smartphone 1 may estimate the outline of the entire abdomen based on an outline less than the semicircular of the abdomen. The smartphone 1 may correct the cross-sectional abdominal image based on the outline of the entire abdomen estimated based on the outline less than the semicircular of the abdomen. The subcutaneous fat and the visceral fat in the abdomen tend to be accumulated in the belly and the ventral, rather than the back. Thus, the smartphone 1 according to the present embodiment may estimate the visceral fat area and the subcutaneous fat area in the abdominal cross-section by measuring the outline including the abdominal portion between the navel and the flank. Alternatively, the smartphone 1 according to the present embodiment may estimate the outline of the entire abdomen by measuring the outline including the abdominal portion between the navel and the flank. Accordingly, the user simply needs to move the smartphone 1 by less than the semicircle of the abdomen at least between the navel and the flank. This further reduces the measurement time.

In the above embodiments, an example in which the outline of the cross-sectional abdominal image of another subject stored in the storage 9 is corrected based on the outline of the abdomen of the user. However, the present disclosure is not limited thereto. For example, the smartphone 1 may correct the user's CT image acquired by measuring the user in the recumbent state stored in the storage 9 based on the outline of the user's abdomen acquired by measuring the user in the upright state.

Many aspects of the disclosure herein may be represented by a series of operations executed by a computer system or other hardware capable of executing a program instruction. The computer system or the other hardware includes, for example, a general-purpose computer, a PC (personal computer), a specialized computer, a workstation, a PCS (Personal Communications System, a personal mobile communication system), a mobile (cellular) phone, a mobile phone having a data processing function, an RFID receiver, a game machine, an electronic notepad, a laptop computer, a GPS (Global Positioning System) receiver, and other programmable data processing apparatuses. Note that in each embodiment the various operations are executed by a dedicated circuit implemented by a program instruction (software) (e.g., discrete logic gates interconnected to perform a specific function), a logical block, a program module or the like executed by at least one processor. The at least one processor for executing the logical block, the program module or the like includes, for example, at least one microprocessor, CPU (Central Processing Unit), ASIC (Application Specific Integrated Circuit), DSP (Digital Signal Processor), PLD (Programmable Logic Device), FPGA (Field Programmable Gate Array), a processor, a controller, a microcontroller, a microprocessor, an electronic device, and other apparatuses designed to be capable of executing the functions described herein, and/or a combination thereof. The embodiments presented herein are implemented by, for example, hardware, software, firmware, middleware, a microcode, or any combination thereof. The instruction may be a program code or a code segment for executing a necessary task. The instruction may be stored in a machine-readable non-transitory storage medium or in another medium. The code segment may represent any combination of a procedure, a function, a subprogram, a program, a routine, a subroutine, a module, a software package, a class or an instruction, and a date configuration or a program statement. The code segment transmits/receives information, a data argument, a variable, and storage contents with another code segment or a hardware circuit. Thus, the code segment is connected to the another code segment or the hardware circuit.

The network used herein includes, unless otherwise specified, the Internet, an ad hoc network, LAN (Local Area Network), Wan (Wide Area Network), MAN (Metropolitan Area Network), a cellular network, WWAN (Wireless Wide Area network), WPAN (Wireless Personal Area Network), PSTN (Public Switched Telephone Network, Terrestrial Wireless Network, other networks, or a combination of any of them. A wireless network includes, for example, an access point (e.g., a Wi-Fi® access point, Wi-Fi is a registered trademark in Japan, other countries, or both), a Femtocell, or the like. Further, a wireless communication device may be connected to a radio network that uses the Wi-Fi, Bluetooth® (Bluetooth is a registered trademark in Japan, other countries, or both), a cellular communication technique such as CDMA (Code Division Multiple Access), TDMA (Time Division Multiple Access), FDMA (Frequency Division Multiple Access), OFDMA (Orthogonal Frequency Division Multiple Access), SC-FDMA (Single-Carrier Frequency Division Multiple Access), or other wireless technologies and/or technical standards. The network may employ one or more technologies such as UTMS (Universal Mobile Telecommunications System), LTE (Long Term Evolution), EV-DO (Evolution-Data Optimized or Evolution-Data Only, GSM® (Global System for Mobile communications, GSM is a registered trademark in Japan, other countries, or both), WiMAX (Worldwide Interoperability for Microwave Access), CDMA-2000 (Code Division Multiple Access-2000), and TD-SCDMA (Time Division Synchronous Code Division Multiple Access).

A circuit configuration of the communication interface and the like provides functionality by using various wireless communication networks such as WWAN, WLAN, WPAN, etc. WWAN may include a CDMA network, a TDMA network, an FDMA network, an OFDMA network, an SC-FDMA network, etc. The CDMA network may be implement by one or more RAT (Radio Access Technology) such as CDMA2000 and Wideband-CDMA (W-CDMA). CDMA2000 includes IS-95, IS-2000 and IS-856 standards. The TDMA network may be implement by GSM® (GMS is a registered trademark in Japan, other countries, or both), D-AMPS (Digital Advanced Phone System), or other RAT. GSM® and W-CDMA are described in documents issued by a consortium called as 3rd Generation Partnership Project (3GPP). CDMA2000 is described in documents issued by a consortium called as 3rd Generation Partnership Project 2 (3GPP2). WLAN may be an IEEE802.11x network. WPAN may be a Bluetooth® network, an IEEE 802.15x network, or other types of network. CDMA can be implemented as a radio technology such as UTRA (Universal Terrestrial Radio Access) or CDMA2000. TDMA can be implemented by wireless technologies such as GSM®/GPRS (General Packet Radio Service)/EDGE (Enhanced Data Rates for GSM® Evolution). OFDMA may be implemented by a radio technology such as IEEE (Institute of Electrical and Electronics Engineers) 802.11 (Wi-Fi), IEEE802.16 (WiMAX), IEEE802.20, E-UTRA (Evolved UTRA), or the like. These technologies can be used for WWAN, WLAN and/or WPAN, and any combination thereof. These technologies may be implemented to use a UMB (Ultra Mobile Broadband) network, an HRPD (High Rate Packet Data) network, a CDMA20001× network, GSM®, LTE (Long-Term Evolution), etc.

The memory used herein may be a computer readable tangible carrier (medium) including a range of a solid-state memory, a magnetic disk, or an optical disk. Such a media stores an appropriate set of computer instructions such as program modules for causing the processor to execute the techniques disclosed herein, or data structures. The computer-readable media includes: electrical connection with one or more wires; a magnetic disk storage; a magnetic cassette; a magnetic tape; another type of magnetic or optical storage device such as CD (Compact Disk), LD® (Laser Disk, LD is a registered trademark in Japan, other countries, or both), DVD® (Digital Versatile disc, DVD is a registered trademark in Japan, other countries, or both), a Floppy® disk (Floppy is a registered trademark in Japan, other countries, or both), and a Blu-ray disc (registered trademark); a portable computer disk; RAM (Random Access Memory); ROM (Read-Only Memory); rewritable and programmable ROM such as EPROM, EEPROM, and a flash memory; other tangible storage media capable of storing information; and any combination of the above. The memory may be provided inside and/or outside a processor/processing unit. As used herein, the term "memory" refers to any types of a long-term memory, a short-term memory, a volatile memory, a nonvolatile memory, or other memories and is not limited to a particular type of memory, a particular number of memories, or a particular medium to store information.

The system disclosed herein includes various modules and/or units for performing specific functions. The modules and the units are schematically illustrated for the purpose of briefly explaining their functionalities. The modules and the units should not be construed as necessarily referring to particular hardware/software. In that sense, the modules, the units, and other components simply need to be hardware and/or software implemented to substantially perform particular functions described herein. Various functions of different elements may be implemented by any combination of hardware/software or by a separated section of the hardware/software, and may be implemented separately or in any combination thereof. An input/output device, an I/O device, or a user interface including such as a keyboard, a display, a touchscreen, a pointing device, and the like may be connected to the system directly or via an intervening I/O controller. As described above, various aspects of the present disclosure may be implemented in many different embodiments, all of which are included within the scope of the present disclosure.

The invention claimed is:

1. An apparatus for generating a cross-sectional abdominal image comprising:
   a memory for provisionally storing a plurality of cross-sectional abdominal images;
   a measuring unit for measuring an outline of an abdomen; and
   a controller configured to correct a cross-sectional abdominal image, corresponding to the outline measured by the measuring unit, of the plurality of cross-sectional abdominal images based on the outline.

2. The apparatus for generating a cross-sectional abdominal image according to claim 1,
   wherein the memory stores the plurality of cross-sectional abdominal images having different ranges of a visceral fat area and a subcutaneous fat area, and
   the controller calculates a shape characteristic from the outline of the abdomen, estimates at least one of the visceral fat area and the subcutaneous fat area of the abdomen based on the shape characteristic, and then selects and corrects the cross-sectional abdominal image corresponding to the estimated at least one of the visceral fat area and the subcutaneous fat area.

3. The apparatus for generating a cross-sectional abdominal image according to claim 1,
   wherein the cross-sectional abdominal image is a CT image acquired in a recumbent state.

4. The apparatus for generating a cross-sectional abdominal image according to claim 1,
   wherein the outline of the abdomen is an outline acquired by measuring a subject in an upright state.

5. The apparatus for generating a cross-sectional abdominal image according to claim 1,
   wherein the controller corrects the cross-sectional abdominal image based on an aspect ratio of the outline of the abdomen.

6. The apparatus for generating a cross-sectional abdominal image according to claim 1,
   wherein the controller corrects the cross-sectional abdominal image such that the outline of the cross-sectional abdominal image matches the outline of the abdomen.

7. The apparatus for generating a cross-sectional abdominal image according to claim 1,
   wherein the controller displays the corrected cross-sectional abdominal image on a display.

8. A method for generating a cross-section abdominal image comprising:
   storing, provisionally, a plurality of cross-sectional abdominal images in a memory;
   measuring an outline of an abdomen; and
   correcting, corresponding to the measured outline, the cross-sectional abdominal image of the plurality of cross-sectional abdominal images, based on the measured outline.

9. The method for generating a cross-sectional abdominal image according to claim 8, further comprising:
   storing the plurality of cross-sectional abdominal images having different ranges of a visceral fat area and a subcutaneous fat area;
   calculating a shape characteristic from the outline of the abdomen;
   estimating at least one of the visceral fat area and the subcutaneous fat area of the abdomen based on the shape characteristic; and
   selecting and correcting the cross-sectional abdominal image corresponding to the estimated at least one of the visceral fat area and the subcutaneous fat area.

10. The method for generating a cross-sectional abdominal image according to claim 8,
    wherein the cross-sectional abdominal image is a CT image acquired in a recumbent state.

11. The method for generating a cross-sectional abdominal image according to claim 8,
    wherein the outline of the abdomen is an outline acquired by measuring a subject in an upright state.

12. The method for generating a cross-sectional abdominal image according to claim 8, further comprising correcting the cross-sectional abdominal image based on an aspect ratio of the outline of the abdomen.

13. The method for generating a cross-sectional abdominal image according to claim 8, further comprising correcting the cross-sectional abdominal image such that the outline of the cross-sectional abdominal image matches the outline of the abdomen.

14. The method for generating a cross-sectional abdominal image according to claim 8, further comprising displaying the corrected cross-sectional abdominal image on a display.

* * * * *